(12) United States Patent
Lundman (10) Patent No.: US 7,681,591 B2
(45) Date of Patent: Mar. 23, 2010

(54) IN-LINE SWIVEL FOR INFLATABLE PLUGS

(76) Inventor: Philip L. Lundman, 3631 Fredonia Kohler Dr., Fredonia, WI (US) 53021

( * ) Notice: Subject to any disclaimer, the term of this patent is extended or adjusted under 35 U.S.C. 154(b) by 480 days.

(21) Appl. No.: 11/621,781

(22) Filed: Jan. 10, 2007

(65) Prior Publication Data
US 2008/0163941 A1   Jul. 10, 2008

(51) Int. Cl.
*F15B 13/00* (2006.01)
(52) U.S. Cl. .................. 137/615; 285/127.1; 285/190
(58) Field of Classification Search ............. 137/615; 285/127.1, 145.2, 190
See application file for complete search history.

(56) References Cited

U.S. PATENT DOCUMENTS

| | | | | |
|---|---|---|---|---|
| 1,092,390 A | * | 4/1914 | Ramsey | 285/127.1 |
| 2,073,255 A | * | 3/1937 | Schaetzly | 285/119 |
| 2,459,643 A | * | 1/1949 | Hartley | 285/190 |
| 2,521,001 A | * | 9/1950 | Forker Jr. | 285/181 |
| 2,538,835 A | * | 1/1951 | Harvey et al. | 285/190 |
| 3,088,759 A | * | 5/1963 | Corsette | 285/190 |
| 3,098,662 A | * | 7/1963 | Iversen | 285/18 |
| 3,210,099 A | * | 10/1965 | Franck | 285/190 |
| 3,334,926 A | * | 8/1967 | Faccou | 285/110 |
| 3,714,951 A | | 2/1973 | Lundman | |
| 4,565,222 A | | 1/1986 | Lundman | |
| 4,787,655 A | * | 11/1988 | Gross et al. | 285/127.1 |
| 5,178,422 A | * | 1/1993 | Sekerchak | 285/144.1 |
| 5,901,752 A | | 5/1999 | Lundman | |
| 6,056,325 A | * | 5/2000 | Bernard | 285/39 |
| 6,446,669 B1 | | 9/2002 | Lundman | |
| 6,568,429 B2 | | 5/2003 | Lundman | |
| 6,899,138 B2 | | 5/2005 | Lundman | |

OTHER PUBLICATIONS

Balcrank Service Bulletin SB5001, Jul. 2002, www.balcrank.com.*

* cited by examiner

*Primary Examiner*—John Rivell
*Assistant Examiner*—Craig Price
(74) *Attorney, Agent, or Firm*—Michael Best & Friedrich LLP (57) ABSTRACT

An in-line swivel having a through bore for fluid flow therethrough. In one embodiment, the swivel comprises an inlet member having a first longitudinal axis and an outlet member having a second longitudinal axis. The outlet member is configured to rotate relative to the inlet member. The swivel also comprises a bearing having a third longitudinal axis. The bearing extends through at least a portion of at least one of the inlet member and the outlet member and includes a fluid passage such that the inlet member and the outlet member are in fluid communication through the bearing, and the first axis and the second axis are substantially perpendicular to the third axis.

15 Claims, 7 Drawing Sheets

IN-LINE SWIVEL FOR INFLATABLE PLUGS

FIELD

Embodiments of the invention generally relate to swivels having bores for fluid flow therethrough. More specifically, embodiments of the invention relate to in-line swivels for use with inflatable plugs configured to restrict fluid flow in a conduit.

BACKGROUND

Inflatable plugs are used for plugging conduits, such as sewer lines, gas lines, or oil pipelines, to permit maintenance, facilitate toxic waste containment, or remove blockages. Swivels facilitate insertion of the plugs into the conduits by guiding a fluid-providing pipe or hose around bends or corners.

SUMMARY

The following summary sets forth certain exemplary embodiments of the invention. It does not set forth all such embodiments and is not limiting of embodiments of the invention.

In one embodiment, a swivel configured to enable fluid flow therethrough comprises an inlet member having a first longitudinal axis and an outlet member having a second longitudinal axis. The outlet member is configured to rotate relative to the inlet member. The swivel also comprises a bearing having a third longitudinal axis. The bearing extends through at least a portion of at least one of the inlet member and the outlet member and includes a fluid passage such that the inlet member and the outlet member are in fluid communication through the bearing, and the first longitudinal axis and the second longitudinal axis are substantially perpendicular to the third longitudinal axis.

In another embodiment, a system to restrict fluid flow in a conduit comprises an inflatable plug, a swivel, and a tube. The inflatable plug is insertable into the conduit and has an inflation point. The swivel includes an inlet member having a first longitudinal axis, an outlet member having a second longitudinal axis, and a hollow bearing having a third longitudinal axis. The outlet member is rotatably joined to the inlet member and coupled to the inflation point of the plug. The hollow bearing is receivable by at least one of the inlet member and the outlet member such that the inlet member and the outlet member are in fluid communication through the hollow bearing, and the first longitudinal axis and the second longitudinal axis are substantially perpendicular to the third longitudinal axis. The tube is coupled to the inlet member of the swivel such that, when the outlet member is coupled to the inflation point of the plug and the tube is coupled to the inlet member, the tube is in fluid communication with the plug.

Various embodiments herein can allow smaller and narrower in-line swivel constructions than existing Z-swivels.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein are for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings. In addition, it should be apparent to one skilled in the art that the terms "inlet" and "outlet" are interchangeable and used herein to facilitate discussion with reference to the figures.

Embodiments of the invention relate to swivels, such as in-line swivels, for use with inflatable plugs. A swivel may be termed 'in-line' if an inlet and an outlet of the swivel are in the same plane and are perpendicular to a pivot axis of the swivel. In various embodiments, the swivels are configured to allow fluid flow therethrough. The swivel receives fluid through the inlet and directs the fluid through the outlet, which is rotatable relative to the inlet. In one application, the swivel is coupled to an inflatable plug and a pipe. The swivel facilitates insertion of the plug into a pipeline such that fluid flowing into the plug may flow through the swivel and fill the plug without requiring highly-flexible tubing. The swivel is configured to facilitate navigation of the plug around corners of varying curvature.

Although embodiments herein are described with reference to inflatable plugs for restricting fluid flow in pipelines, the disclosed embodiments are applicable to a host of other fluid flow applications. For example, the disclosed swivels may be adapted for hydraulic lines in heavy machinery such as cranes, backhoes, and snowplows. In addition, the swivels may be configured for medical applications where it is necessary to traverse body cavities or blood vessels with, for example, catheters or stents.

Figure 1:
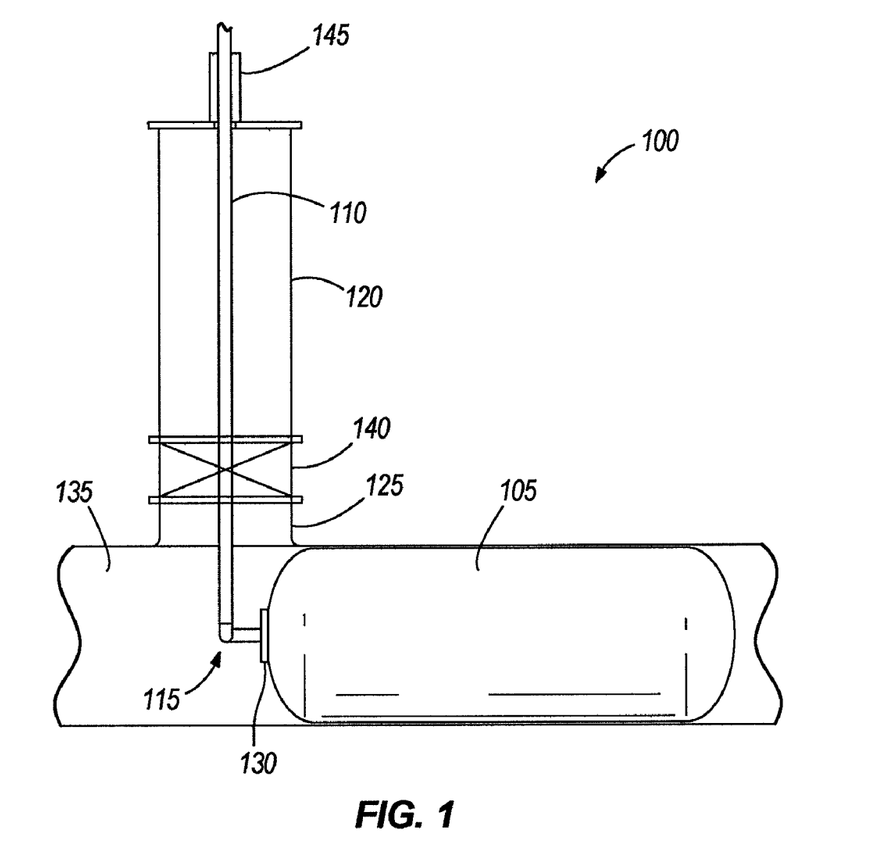
FIG. 1 shows a system according to an embodiment of the invention.

FIG. 1 shows a system 100 according to an embodiment of the invention. The system 100 includes an inflatable plug 105, a tube 110, an in-line swivel 115, a launch cylinder 120, a tapping saddle 125, and a tapping valve 140. The system 100 is configured for use in a conduit 135, which may be, for example, a sewer pipe or an oil pipeline. In the illustrated embodiment, the plug 105 is inflated to fill the inside of the conduit 135 and thereby restrict fluid flow through the conduit 135.

The tapping saddle 125 and the tapping valve 140 (e.g., a port valve) couple to the conduit 135 by bolts, welding, or electro-fusion. The tapping saddle 125 and the tapping valve 140 allow selective access to the interior of the conduit 135 through a hole formed thereon. The tapping valve 140 allows pressure equalization in the launch cylinder 120 after the launch cylinder 120 is coupled to the tapping valve 140. The launch cylinder 120 guides the tube 110 (which may be, for example, an inflation ram) and the deflated plug 105 into the interior of the conduit 135. A packing seal 145 is positioned around the tube 110 to prevent fluid in the conduit 135 from leaking out through the launch cylinder 120.

The tube 110 is in fluid communication with the plug 105 via the swivel 115. An inlet of the swivel 115 couples to one end of the tube 110 and directs fluid toward the plug 105. An outlet of the swivel 115 couples to an inflation point 130 (e.g., port, valve, flange, etc.) of the plug 105 to allow the fluid to enter and inflate the plug 105. The fluid may be, for example, air, nitrogen, water, or other liquids and gases suitable for inflation of the plug 105.

The system 100 is also configured to allow for deflation of the plug 105. The fluid may be drawn from the plug 105, through the swivel 115, and into the tube 110. In such a configuration, the outlet of the swivel 115 may be considered the inlet, and vice versa.

In some embodiments, the inlet and the outlet of the swivel 115 may include internal threading to facilitate coupling to the tube 110 and the plug 105. Alternatively or additionally, the inlet and the outlet may include fasteners (e.g., screws, snap rings, clamps, quick connect/disconnect fittings, etc.) to facilitate coupling.

The swivel 115 may be made from metal, plastic, or other appropriate materials. In addition, the swivel 115 may be manufactured by injection molding, machining, or pressing. In the embodiment illustrated in FIG. 1, the swivel 115 directs the fluid toward the plug 105 at about a 90 degree angle. The swivel 115 is constructed to allow for about 90 degrees of rotation or pivoting of the outlet relative to the inlet in either direction. In other embodiments, the swivel 115 may be adapted to allow for a greater or lesser angle of rotation, or may only allow rotation in one direction. Various embodiments of the swivel 115 are described in more detail below.

Figure 2:
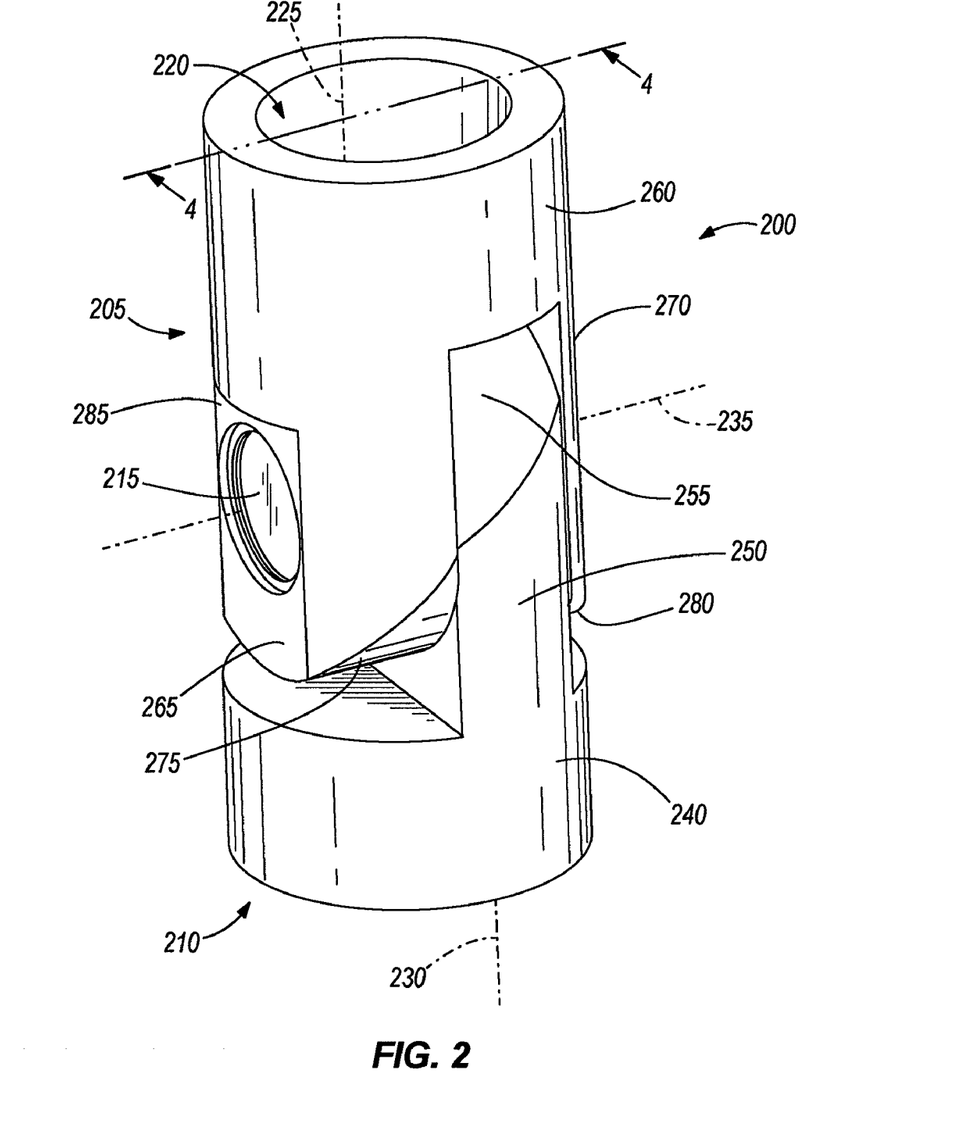
FIG. 2 shows a perspective view of a swivel according to an embodiment of the invention.

FIG. 2 shows a perspective view of a swivel 200 according to an embodiment of the invention. The swivel 200 is one implementation of the swivel 115 of FIG. 1. The swivel 200 includes an inlet member 205, an outlet member 210, and a hollow bearing 215. The outlet member 210 includes a cylindrical base 240 and a central projection 250. The central projection 250 is generally rectangular and includes an upper edge 255 having a rounded surface. The central projection 250 extends from the cylindrical base 240 between a first flat surface 345 and a second flat surface 350 (see FIG. 3).

The inlet member 205 includes a cylindrical base 260, a first leg 265, and a second leg 270 spaced apart from the first leg 265. The first and second legs 265, 270 extend from the cylindrical base 260 and define a generally rectangular notch 355 (see FIG. 3) therebetween. The notch 355 is sized and shaped to snugly receive the central projection 250 of the outlet member 210 so that substantially no gap exists between the legs 265, 270 and the projection 250. A lower edge 275 of the first leg 265 and a lower edge 280 of the second leg 270 are rounded such that the swivel 200 may rotate (e.g., pivot) without the lower edges 275, 280 contacting the flat surfaces 345, 350.

Rotation of the outlet member 210 facilitates directing the plug 105 around bends or corners. In the illustrated embodiment, an outlet 400 of the outlet member 210 (see FIG. 4) is operable to rotate about 90 degrees in either direction relative to an inlet 220 of the inlet member 205. During operation, the fluid flows in the inlet 220, through the bearing 215, and out the outlet 400.

The inlet member 205 has a first longitudinal axis 225 extending therethrough, the outlet member 210 has a second longitudinal axis 230 extending therethrough, and the bearing 215 has a third longitudinal axis 235 extending perpendicular to the first and second longitudinal axes 225, 230. The inlet member 205 includes an exterior surface 207 that is generally parallel to the first longitudinal axis 225 (see FIG. 4). The outlet member 210 includes an exterior surface 212 that is collinear with the exterior surface 207 of the inlet member 205 and is generally parallel to the second longitudinal axis 230 (see FIG. 4). Due to the rotation of the outlet member 210 relative to the inlet member 205, the third longitudinal axis 235 may, in some embodiments, be regarded as a pivot axis. The swivel 200 is configured such that during rotation of the outlet member 210 about the bearing 215 relative to the inlet member 205, the perpendicular relationship between the first and second longitudinal axes 225, 230 and the third longitudinal axis 235 is maintained regardless of the orientation of the outlet 400 relative to the inlet 220.

Figure 3:
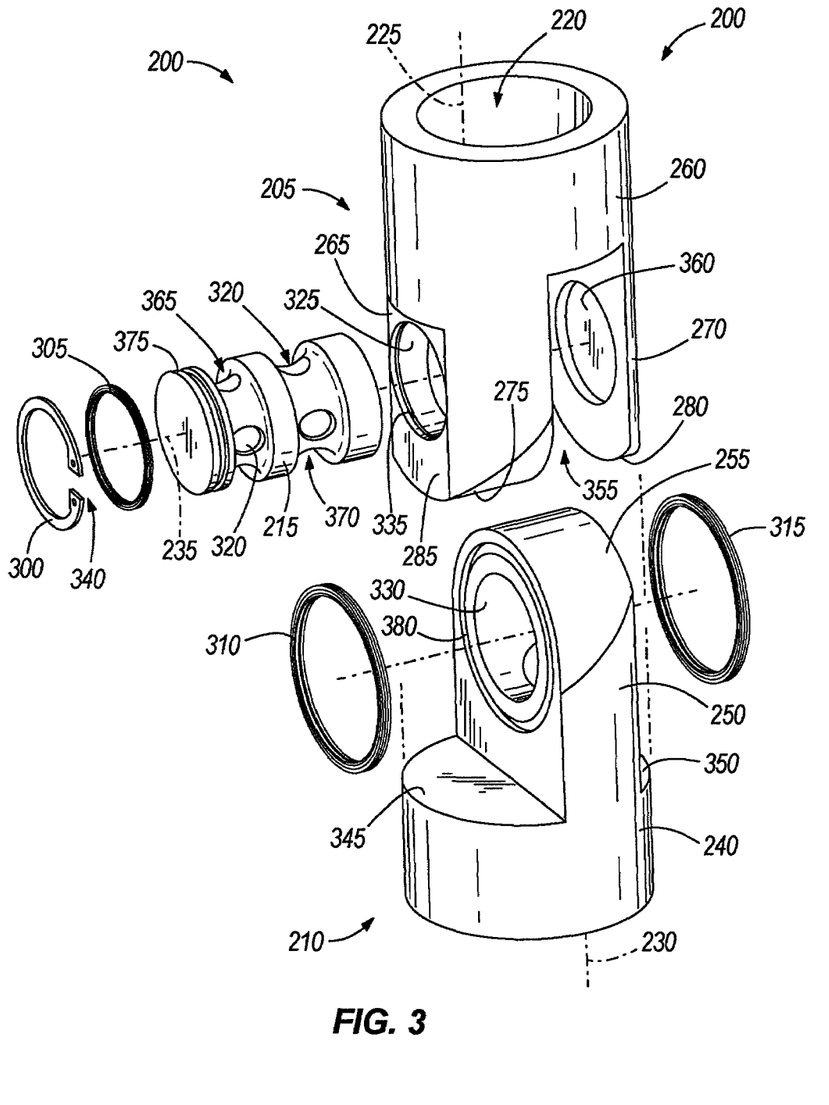
FIG. 3 shows an exploded view of the swivel of FIG. 2.
Figure 4:
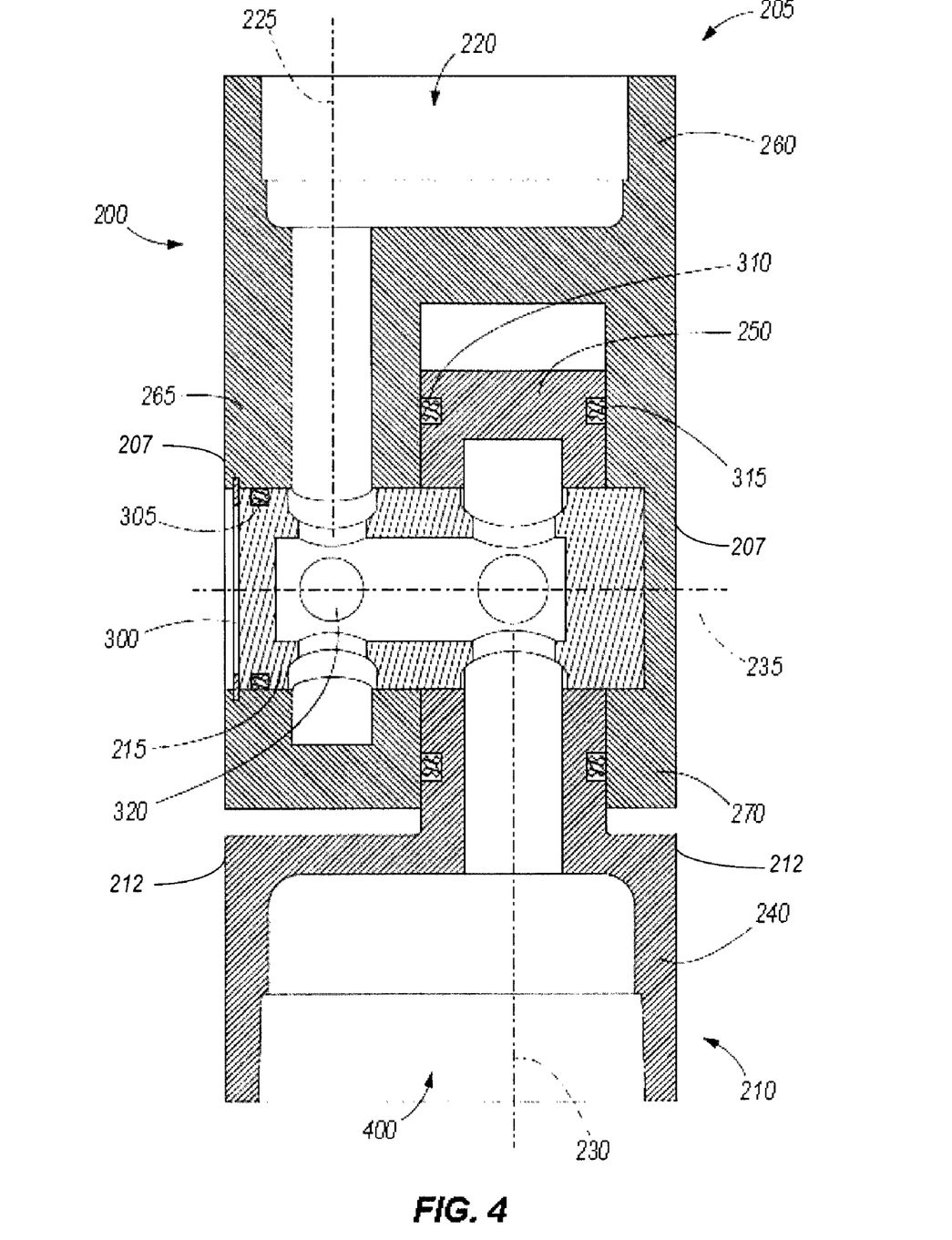
FIG. 4 shows a cross-sectional view of the swivel taken along line 4-4 of FIG. 2.

FIG. 3 shows an exploded view of the swivel 200 of FIG. 2, and FIG. 4 shows a cross-sectional view of the swivel 200 of FIG. 2. As shown, the swivel 200 includes a retaining ring 300 and three sealing members 305, 310, 315. In the illustrated embodiment, the sealing members 305, 310, 315 are rubber X-rings. In other embodiments, the sealing members 305, 310, 315 may be O-rings or other suitable annular seals.

The bearing 215 shown is a generally cylindrical member and is slidably received through a bore 325 in the first leg 265 of the inlet member 205 and a bore 330 in the central projection 250 of the outlet member 210. A cylindrical recess 360 formed on an interior wall of the second leg 270 is sized to receive a portion of the bearing 215. The inlet member 205 and the outlet member 210 receive the bearing 215 such that the bearing 215 does not extend past an exterior flat surface 285 of the inlet member 205. In the embodiment illustrated in FIG. 4, the bearing 215 is partially recessed relative to the outside surface of the inlet member 205.

The bearing includes a first track 365 and a second track 370 axially spaced apart from the first track 365. The first track 365 is a concave portion extending around the bearing 215 and is aligned with the first leg 265 of the inlet member 205. The second track 370 is a concave portion extending around the bearing 215 and is aligned with the central projection 250 of the outlet member 210. Apertures 320 are spaced apart within the first track 365 and the second track 370 such that fluid flowing in the inlet member 205 may flow around the first track 365, through one or more of the apertures 320 in the first track 365, through an interior of the bearing 215, out one or more of the apertures 320 in the second track 370, around the second track 370, and out the outlet member 210. Therefore, the first and second tracks 365, 370 and the apertures 320 maintain fluid communication between the inlet 220 and the outlet 400 regardless of the orientation of the outlet member 210 and the bearing 215 relative to the inlet member 205.

The retaining ring 300 is positioned about a groove 335 in the bore 325 of the inlet member 205 to prevent the bearing 215 from sliding out of the bores 325, 330 of the inlet member 205 and the outlet member 210. The retaining ring 300 includes a gap 340 which may be closed (e.g., squeezed together) so that the diameter of the retaining ring 300 decreases. Decreasing the diameter allows the retaining ring 300 to enter the bore 325 of the inlet member 210. The gap 340 may then be opened (e.g., spread apart) so that the diameter of the retaining ring 300 increases to securely mount in the groove 335. Removal of the retaining ring 300 allows disassembly of the inlet member 205, the outlet member 210, and the bearing 215. Disassembly may be desirable for cleaning of the swivel 200 or replacement of the sealing members 305, 310, 315.

The sealing members 305, 310, 315 are positioned inside the swivel 200. One sealing member 305 is positioned in a groove 375 on an end of the bearing 215 adjacent to the retaining ring 300. The other sealing members 310, 315 are positioned in grooves 380 on opposing sides of the central projection 250 of the outlet member 210 adjacent to the bore 330. The sealing members 305, 310, 315 provide a seal such that fluid may not enter or exit the swivel 200 at interfaces between the inlet member 205, the outlet member 210, and the bearing 215.

Figure 5:
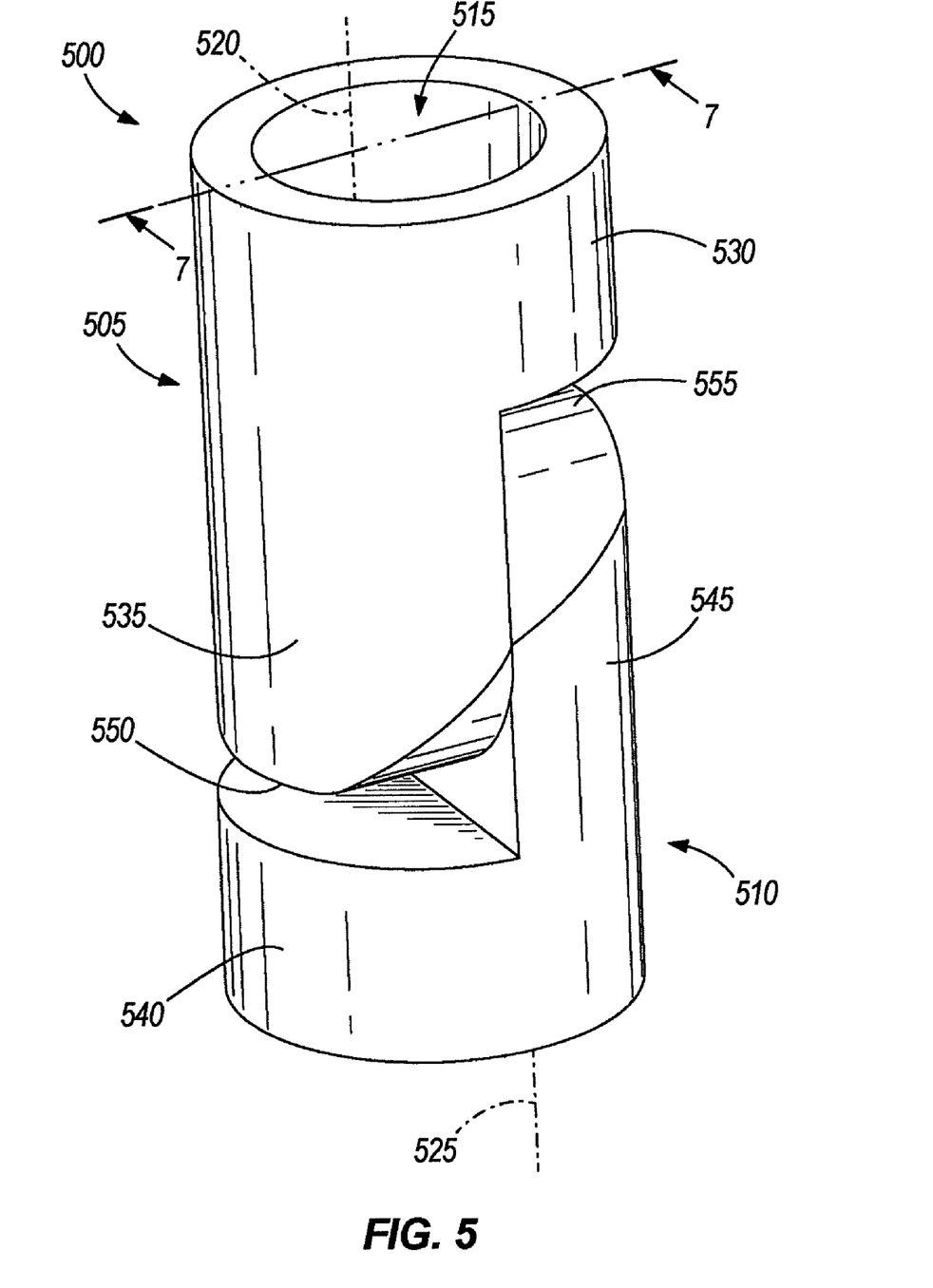
FIG. 5 shows a perspective view of a swivel according to another embodiment of the invention.

FIG. 5 shows a perspective view of a swivel 500 according to another embodiment of the invention. The swivel 500 is another implementation of the swivel 115 of FIG. 1 and functions in a similar manner to that of the swivel 200 described with regards to FIGS. 2-4. The swivel 500 includes an inlet member 505 and an outlet member 510. The inlet member 505 includes an inlet cylindrical base 530 and an inlet leg 535 extending from the inlet base 530. The outlet member 510 includes an outlet cylindrical base 540 and an outlet leg 545 extending from the outlet base 540. The outlet member 510 is rotatably coupled to the inlet member 505 such that the outlet leg 545 is adjacent to the inlet leg 535. In addition, a rounded surface 550 of the inlet leg 535 is adjacent to and within the profile of a flat surface 640 (see FIG. 6) of the outlet base 540. A rounded surface 555 of the outlet leg 545 is likewise adjacent to and within the profile of a flat surface 635 (see FIG. 6) of the inlet base 530.

The outlet member 510 may rotate (e.g., pivot) relative to the inlet member 505 to facilitate insertion of the plug 105 around bends or corners. In the illustrated embodiment, an outlet 705 of the outlet member 510 (see FIG. 7) is operable to rotate about 90 degrees in either direction relative to an inlet 515 of the inlet member 505. During operation, the fluid flows in the inlet 520, through the swivel 500, and out the outlet 705.

Figure 6:
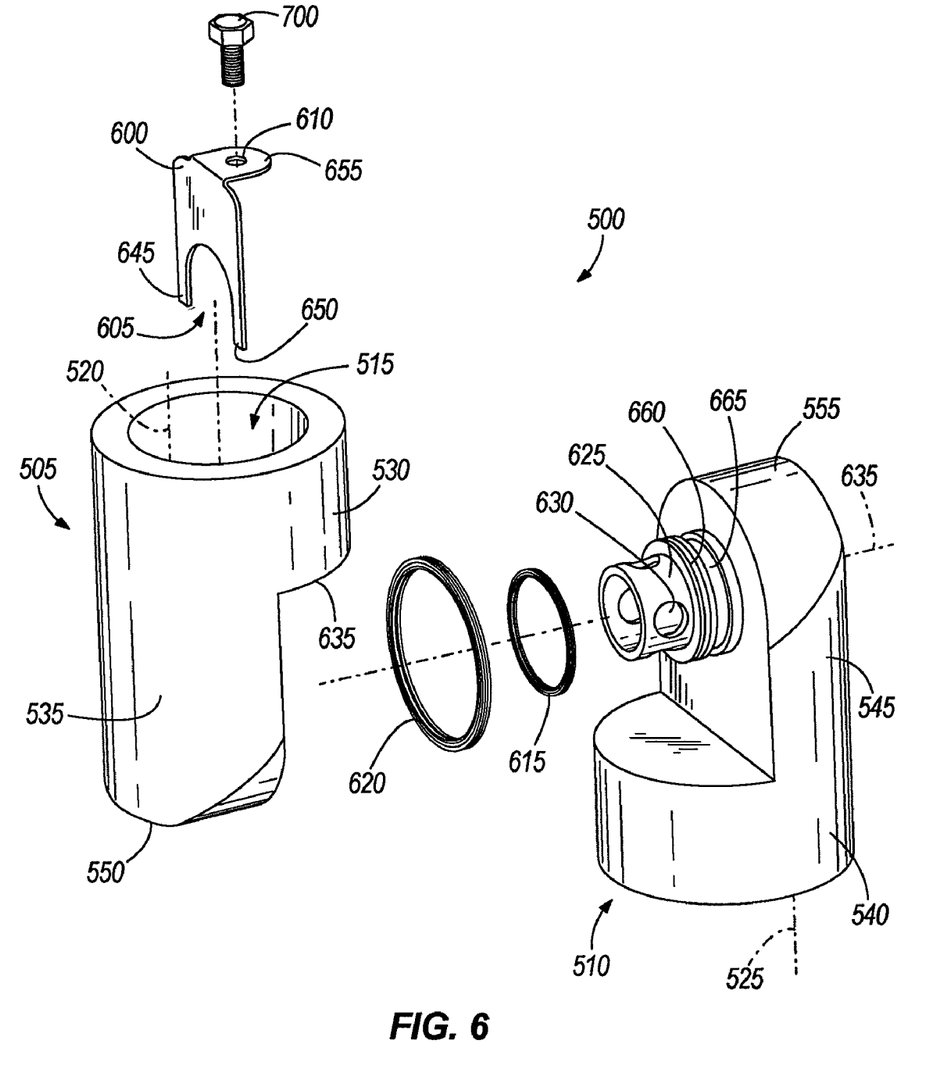
FIG. 6 shows an exploded view of the swivel of FIG. 5.
Figure 7:
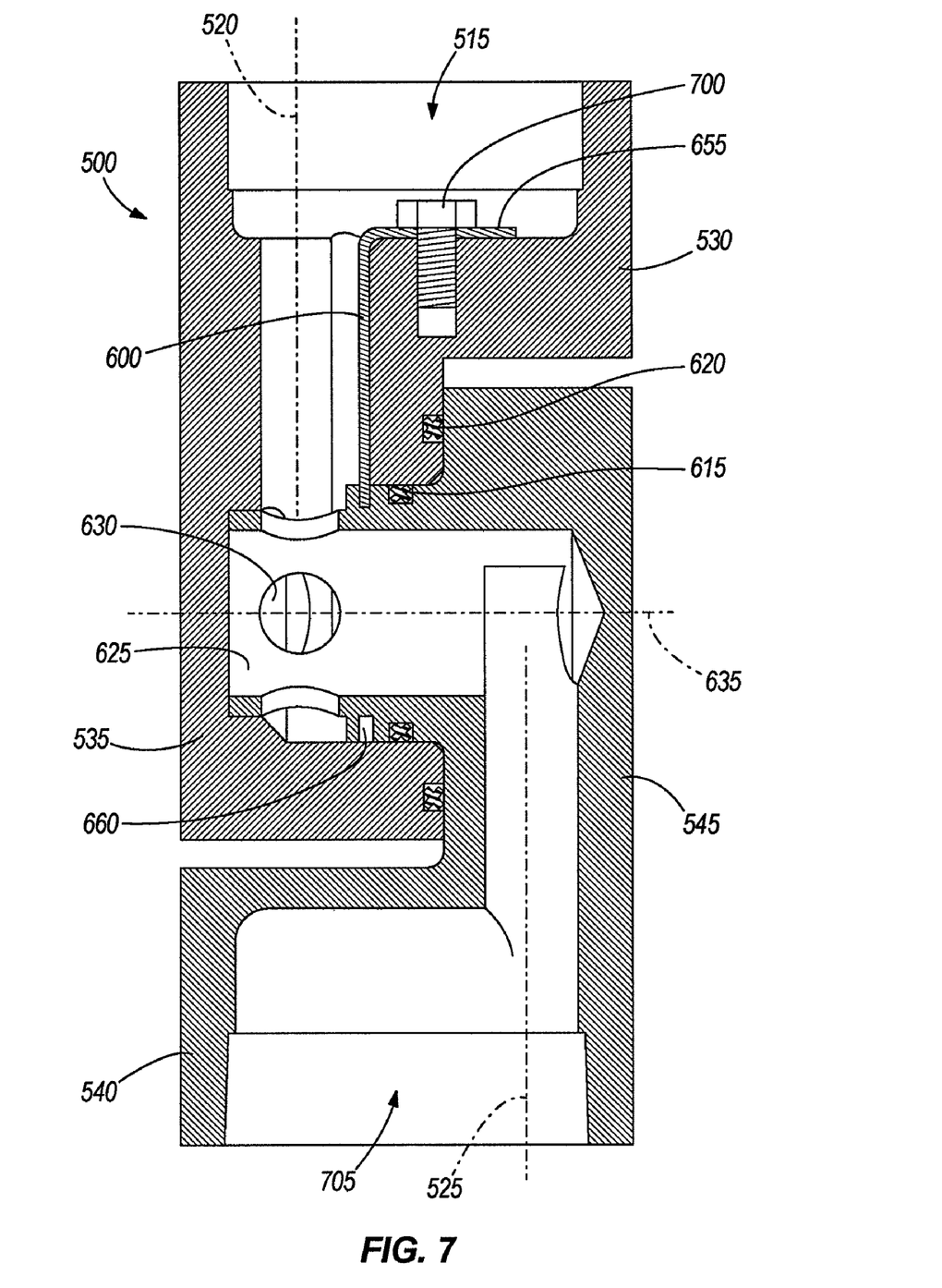
FIG. 7 shows a cross-sectional view of the swivel taken along line 7-7 of FIG. 5.

FIG. 6 shows an exploded view of the swivel 500 of FIG. 5, and FIG. 7 shows a cross-sectional view of the swivel 500 of FIG. 5. In the embodiment shown, the swivel 500 includes a retaining member 600 and two sealing members 615, 620. The outlet member 510 includes a hollow bearing 625 extending perpendicularly from the outlet leg 545. The bearing 625 is an integral piece of the outlet member 510, forming a single unitary structure. The bearing 625 is receivable by the inlet member 505 to rotatably couple the outlet member 510 to the inlet member 505. In other embodiments, the bearing 625 may be an integral piece of the inlet member 505 and, as such, receivable by the outlet member 510. In the embodiment illustrated in FIGS. 6 and 7, the bearing 625 includes a plurality of apertures 630 and is partially received within a cylindrical recess formed on an interior wall of the inlet leg 535. The apertures 630 are positioned around the bearing 625 such that fluid flowing in the inlet member 505 may flow through one or more of the apertures 630, through an interior of the bearing 625, and out the outlet member 510.

The inlet member 505 has a first longitudinal axis 520 extending therethrough, the outlet member 510 has a second longitudinal axis 525 extending therethrough, and the bearing 625 has a third longitudinal axis 635 extending perpendicular to the first and second longitudinal axes 520, 525. Due to the rotation of the outlet member 510 relative to the inlet member 505, the third longitudinal axis 635 may, in some embodiments, be regarded as a pivot axis. Similar to the previous embodiment of FIGS. 2-4, the swivel 500 is configured such that during rotation of the outlet member 510 and the bearing 625 relative to the inlet member 505, the perpendicular relationship between the first and second longitudinal axes 520, 525 and the third longitudinal axis 635 is maintained.

The retaining member 600 is positioned inside the inlet member 505 to secure the bearing 625 and the outlet member 510 to the inlet member 505. The retaining member 600 includes a first arm 645, a second arm 650, and a head 655. The first and second arms 645, 650 define an arch having a notch 605 to partially surround the bearing 625. In the embodiment illustrated in FIGS. 6 and 7, the notch 605 aligns the first and second arms 645, 650 within a groove 660 in the bearing 625 to prevent axial separation of the inlet member 505 and the outlet member 510.

The head 655 extends from the retaining member 600 generally perpendicular to the first and second arms 645, 650 and includes a bore 610 to receive a fastener 700 (e.g., screw, bolt, nail, etc.). The fastener 700 removably couples the retaining member 600 to the inlet member 505 such that the fastener 700 and the retaining member 600 may be removed to allow disassembly of the swivel 500.

One sealing member 615 is positioned in a groove 665 about the bearing 625 adjacent to the inlet member 505. The other sealing member 620 is positioned in a groove on the inlet leg 535 between the inlet leg 535 and the outlet leg 545. In the illustrated embodiment, the sealing members 615, 620 are rubber X-rings. In other embodiments, the sealing members 615, 620 may be O-rings or other suitable annular seals. The sealing members 615, 620 provide a seal such that fluid may not enter or exit the swivel 500 at interfaces between the inlet member 505 and the outlet member 510.

In some embodiments, a swivel may include a valve to regulate the flow of fluid therethrough. The valve may be, for example, a check valve to only allow unidirectional fluid flow, a solenoid to allow selective flow, or a throttling valve to control the volume of fluid flow. Furthermore, the inlet and the outlet of the swivel may have different diameters to provide a throttling condition.

Embodiments described above do not require an exterior elbow, allowing the swivels to operate with only one interior right angle bend to direct fluid flow. As such, embodiments herein are more compact and narrower compared to existing Z-swivels, allowing holes for tapping into conduits to be smaller.

Various features and advantages of the invention are set forth in the following claims.

What is claimed is:

1. A swivel configured to enable fluid flow therethrough, the swivel comprising:
   an inlet member having a first longitudinal axis;
   an outlet member rotatable relative to the inlet member and having a second longitudinal axis; and
   a bearing extending through at least a portion of at least one of the inlet member and the outlet member, the bearing including a fluid passage such that the inlet member and the outlet member are in fluid communication through the bearing, the bearing having a third longitudinal axis, wherein the first axis and the second axis are substantially perpendicular to the third axis, and
   wherein the bearing is positioned within the at least one of the inlet member and the outlet member such that the bearing does not extend along the third axis past an exterior surface of the inlet member and a collinear exterior surface of the outlet member, the exterior surface of the inlet member being generally parallel to the first longitudinal axis and the exterior surface of the outlet member being generally parallel to the second longitudinal axis.

2. The swivel of claim 1, and further comprising a sealing member positioned around the bearing.

3. The swivel of claim 1, and further comprising a sealing member positioned between the inlet member and the outlet member.

4. The swivel of claim 1, wherein the bearing is integrally formed with one of the inlet member and the outlet member.

5. The swivel of claim 1, wherein the bearing includes a plurality of apertures, such that when the outlet member rotates relative to the inlet member, the outlet member is in fluid communication with the inlet member.

6. The swivel of claim 1, and further comprising a retainer positioned at least partially around the bearing and coupled to the inlet member.

7. The swivel of claim 1, wherein the inlet member is configured to be coupled to a tube configured to supply fluid to the swivel.

8. The swivel of claim 1, wherein the outlet member is configured to be coupled to an inflatable plug.

9. A system to restrict fluid flow in a conduit, the system comprising:
   an inflatable plug insertable into the conduit and having an inflation point;
   a swivel including
      an inlet member having a first longitudinal axis,
      an outlet member rotatably joined to the inlet member and coupled to the inflation point of the plug, the outlet member having a second longitudinal axis, and
      a hollow bearing receivable by at least one of the inlet member and the outlet member such that the inlet member and the outlet member are in fluid communication through the hollow bearing, the hollow bearing having a third longitudinal axis, wherein the first axis and the second axis are substantially perpendicular to the third axis, and
   wherein the bearing is positioned within the at least one of the inlet member and the outlet member such that the bearing does not extend past an exterior surface of the inlet member and a collinear exterior surface of the outlet member, the exterior surface of the inlet member being substantially parallel to the first longitudinal axis and the exterior surface of the outlet member being substantially parallel to the second longitudinal axis; and
   a tube coupled to the inlet member of the swivel,
   wherein, when the outlet member is coupled to the inflation point of the plug, and when the tube is coupled to the inlet member, the tube is in fluid communication with the plug.

10. The system of claim 9, wherein the conduit is a pipe.

11. The system of claim 9, and further comprising a sealing member positioned around the bearing.

12. The system of claim 9, and further comprising a sealing member positioned between the inlet member and the outlet member.

13. The system of claim 9, wherein the bearing is integrally formed with one of the inlet member and the outlet member.

14. The system of claim 9, wherein the bearing includes a plurality of apertures, such that when the outlet member rotates relative to the inlet member, the outlet member is in fluid communication with the inlet member.

15. The system of claim 9, and further comprising a retainer positioned at least partially around the bearing and coupled to the inlet member.

* * * * *